United States Patent [19]

Nakamura et al.

[11] Patent Number: 4,568,444
[45] Date of Patent: Feb. 4, 1986

[54] CHEMICAL SUBSTANCE MEASURING APPARATUS

[75] Inventors: Michihiro Nakamura, Soja; Makoto Yano, Kurashiki; Hidehiko Ikeya, Kurashiki; Hiroshi Tsurumi, Kurashiki; Osamu Kusudo, Kurashiki; Yoshito Hamamoto, Kurashiki, all of Japan

[73] Assignee: Kuraray Co., Ltd., Kurashiki, Japan

[21] Appl. No.: 724,641

[22] Filed: Apr. 18, 1985

[30] Foreign Application Priority Data

Apr. 30, 1984 [JP] Japan ................................. 59-88185

[51] Int. Cl.⁴ ...................... G01N 27/30; G01N 27/50
[52] U.S. Cl. .................................. 204/412; 128/635; 204/403; 204/416; 204/435; 357/25
[58] Field of Search .............. 204/435, 412, 416, 418, 204/419, 420, 403; 128/635; 357/25

[56] References Cited

U.S. PATENT DOCUMENTS

| | | | |
|---|---|---|---|
| 3,461,055 | 8/1969 | Staunton | 204/435 |
| 3,709,810 | 1/1973 | Grubb et al. | 204/435 X |
| 3,833,495 | 9/1974 | Grubb | 204/435 X |
| 3,880,737 | 4/1975 | Brunt | 204/435 X |

FOREIGN PATENT DOCUMENTS 120942 9/1981 Japan ................................. 204/416

Primary Examiner—G. L. Kaplan
Attorney, Agent, or Firm—Oblon, Fisher, Spivak, McClelland & Maier

[57] ABSTRACT

An apparatus for measuring the quantities of chemical substances contained in a solution to be assayed by using a chemical-substance sensitive sensor consists of a potentiometric electrode which responds selectively to chemical substances, and a liquid-junction type reference electrode including a tube, a porous thread member housed in the front end opening of the tube and having a pore capacity of 0.2 cc/g or more and at least the surface of which is hydrophilic, a silver-silver chloride wire is provided and housed in the tube so that at one end of the wire is in contact with the thread member and the wire which extends along the tube. The wire is connected to a connector at the other end opening of the tube, an electrical insulating resin fills said tube, at least at the front end portion thereof, for fixing both the silver-silver chloride wire and the thread member by contact therewith and for stopping said tube. An internal solution is retained by suction in said porous thread member. This apparatus is advantageously used for monitoring the living body and may be thermally sterilized.

13 Claims, 6 Drawing Figures

CHEMICAL SUBSTANCE MEASURING APPARATUS

BACKGROUND OF THE INVENTION

1. Field of the Invention

The present invention relates to an apparatus for measuring the quantities of chemical substances contained in a solution to be assayed by using a chemical-substance sensitive sensor consisting of a potentiometric electrode which responds selectively to chemical substances, and a liquid-junction type reference electrode.

2. Description of Prior Art

Recently, in the physiological and medical fields, measurements are frequently made of the concentration of substances contained in the body fluids represented by the blood, for example ions such as hydronium ion, sodium ion, potassium ion, calcium ion, and chloride ion; gases such as oxygen and carbon dioxide; sugar such as glucose and lactose; and chemical substances such as hormones, enzymes, and antibodies. Various types of potentiometric electrodes have been used in the past. For the measurement of such chemical substances such as devices employing a glass electrode, a coated-wire electrode, and chemically modified metal electrode. Glass electrodes, in particular, are widely used, since they can be adapted to respond selectively to various kinds of chemical substances by changing the composition of the glass membrane or coating a chemically sensitive film on the glass membrane. However, the miniaturization of a glass electrode for the determination of the local amount of chemical substances in a tissue of a living body involves problems in that reduced strength of the glass membrane results and also in increased resistance of the glass membrane, which naturally leads to a decrease in the response speed.

As a miniature ion sensor capable of solving the aforesaid problem with such glass electrode, an ion sensor utilizing the field effect of semiconductors has been proposed in U.S. Pat. No. 4,020,830 and U.S. Pat. No. 4,218,298. This ion sensor is called ISFET (Ion Sensitive Field Effect Transistor). The boundary electric potential appearing on the surface of the ion sensitive membrane of said ISFET is dependent upon the activity of the specific ions contained in the solution to be assayed. A change in the boundary electric potential leads to a corresponding change in the conductivity of the channel under the ion sensitive membrane, if the electric potential of the solution is kept constant by means of a reference electrode. Where such principle is applied in detecting a boundary electric potential, the problem of electrode resistance as experienced with the conventional glass electrode is solved the output impedance involved is low by virtue of the impedance converting function of the ISFET; therefore, a high-input impedance amplifier as an external circuit is not required. This new-type ion sensor has the following characteristics:

(1) Since it involves little problem, if any, of electrode resistance, the ion sensor can be miniaturized so as for it to be inserted into a living body and is able to respond fast.

The IC technique used permits integration (multiplexing) of various types of ion sensors on one silicon chip.

(3) It is suitable for mass production.

Because of these characteristics the ISFET, as a sensor for monitoring the quantity of chemical substances in a living body by inserting it into the tissue of the body, is attracting wide attention. Further, it is known that the ISFET can be adapted to respond to various kinds of substances by modifying its ion-sensitive membrane. For example, there are the following types of ISFET: a pH sensor using silicon nitride, alumina, or tantalum pentoxide for the sensitive membrane; a cation ($Na^+$, $K^+$ or the like) sensor using an inorganic glass membrane; a chloride ion sensor having a sensitive membrane of an inorganic compound such as AgCl; an ion ($Na^+$, $K^+$, $Ca^{++}$ or the like) sensor having a sensitive membrane formed of a polymer matrix, such as polyvinyl chloride or silicone resin, and crown ether, phosphate, or the like added or fixed thereto; and such other sensors for measuring substrates and immune substances as enzyme sensor and immuno-sensor, which comprise a combination of any of above named sensors and an enzyme membrane, an antibody or antigen.

An electric circuit as shown in FIG. 1 is usually employed in measuring the concentration of ions contained in the solution to be assayed by means of such ion sensor. An ISFET 1, together with a liquid-junction reference electrode 4, is immersed in the to-be-assayed solution 8 in a receptacle 6. To a drain terminal 2 of the ISFET is connected the positive potential of a voltage source Vd, and to its source terminal 3 is connected a constant current source 5. The ISFET operates through a source follower circuit thus formed. Any change in the conductivity of the channel under the ion sensitive membrane that results from a change in the boundary electric potential between the membrane 7 and the to-be-assayed solution 8 is drawn in terms of source potential Vs. Since the source potential Vs is in linear relation to a logarithm of ion concentration, it is possible to measure the concentration of ions contained in the solution being assayed by determining the source potential Vs.

In order to measure the quantity of chemical substances contained in the solution being assayed by using said ISFET or the conventional glass electrode as a potentiometric electrode for chemical-substance measurement, there must be a reference electrode having a constant potential in its interface with the being-assayed solution regardless of the composition of the solution. Therefore, the reference electrode is of such construction that the to-be-assayed solution may be brought into contact with an internal solution housed in a closed tube and having a constant composition, through a small space called liquid junction which is provided at front end of the tube. In the internal solution within the tube there is immersed an internal electrode such as Ag-AgCl electrode.

A reference electrode used together with ion sensors, such as ISFET, particularly for the purpose of living-body monitoring must be miniaturized enough to be insertible in a living body and must be steam-autoclavable. In the case of a combined-type sensor having an ion sensor and a reference electrode housed together in one tube, it is required that the reference electrode be further miniaturized. However, the smaller the reference electrode in size, the less is the quantity of the internal solution housed in the tube. In a prolonged measurement operation, therefore, it is very important to prevent the outflow of the internal solution. In order to reduce the flowout of the internal solution, there has been proposed a reference electrode having its liquid junction comprised of an acetyl cellulose membrane or ceramic which is permeable to water and ions and yet retards the diffusion thereof. Such reference electrode has the advantage that the outflow of the internal solution during a measurement operation can be reduced, but on the other hand it has the following difficulties during steam autoclavation (which is usually carried out in a hot, high-pressure steam atmosphere at about 120° C. for approximately 20 minutes):

(1) that the internal solution flows out in the course of steam autoclavation; and (2) that air dissolved in the internal solution adheres to the surface of the internal electrode in the form of bubbles, or interrupts the conduction between the internal electrode and the solution being assayed, which leads to an increased electric resistance between the solution and the internal electrode and causing instability of the reference electrode potential.

In order to overcome these difficulties, a usual practice is that an internal solution steam-autoclaved before use is placed in the tube in which the internal electrode is housed. While the difficulties discussed involved in above with respect to and steam autoclavation can be overcome, this practice is not desirable since it involves the possibilities that the effect of sterilization may be impaired unless extreme care is used when the sterilized internal solution is placed into the tube, care must be taken to prevent air from being mixed into the internal solution when the latter. It is also known to use sols of agar-agar, gelatine, polyvinyl alcohol, polyhydroxymethyl methacrylate, and the like, or hydrogels of hyperfine silica and the like, for the internal solution in order to prevent the outflow of the internal solution during measurement. Such reference electrode having such sol or hydrogel contained therein as the internal solution involves maintenance difficulties, though it is effective to some extent for the prevention of outflow of the internal solution in the course of measurement and also for the prevention of bubble generation in the internal solution during storage. Further, sols of organic polymers such as, for example, agar-agar, gelatine, polyvinyl alcohol, and polyhydroxy methacrylate, when heated, produce a potassium permanganate reducing substance which may be hazardous to living bodies. Polyhydroxyethyl methacrylate sol cannot be used as the internal solution because it is liable to separate into a polymer phase and a water phase upon heating. Hyperfine silica hydrogel is so high in viscosity that it is difficult, if not impossible, to put the gel into the tube.

In view of these facts, the present inventors proposed in Japanese Published Unexamined Patent Application No. 204363/1983 a steam autoclavable, miniaturized liquid-junction type reference electrode having its internal solution gelled by a high polymer.

Said reference electrode comprises: a one piece tube, an internal solution housed in this tube and gelled by 2~10% by weight of polyvinyl alcohol and 0.1~2% by weight of a crosslinking agent selected from the group consisting of titanium compounds, zirconium compounds, and vanadium compounds, an internal electrode immersed in the internal solution, and a liquid junction provided in the front end portion of the tube and with communicating between the inside of the tube and the outside thereof.

However, subsequent studies made with said reference electrode, in which aforesaid polymeric gel was used as a holder for the internal solution, revealed that the reference electrode still involved a number of problems yet to be solved, as enumerated below.

(1) During storage or steam autoclavation, bubbles in the polymeric gel aggregate into larger bubbles, whereby the electric connection between the internal electrode and the solution to be assayed is broken.

(2) Use of the polymeric gel as the holder for the internal solution causes a large liquid junction potential, with the result that the potential of the reference electrode varies according to the composition of the solution to be assayed.

(3) The manufacture of the reference electrode is complicated because the internal solution has to be gelled by the polymer and crosslinking agent in the reference electrode.

SUMMARY OF THE INVENTION

Accordingly, it is an object of this invention to provide a chemical-substance measuring apparatus incorporating a liquid-junction type reference electrode which is free from the possibility of the electric connection being broken during a steam autoclaving operation.

It is another object of the invention to provide a steam-autoclavable chemical substance measuring apparatus in which a chemical-substance sensitive sensor consisting of a potentiometric electrode which responds selectively to specific chemical substances, and a liquid-junction type reference electrode are housed in one tube.

It is a further object of the invention to provide a chemical-substance measuring apparatus incorporating a steam-autoclavable reference electrode having an internal-solution holder free from the possibility of elution of such substances harmful to living bodies as toxic substances, pyrogens, and potassium permanganate reducing substances.

The chemical-substance measuring apparatus for measuring the quantities of chemical substances contained in a solution to be assayed in accordance with the invention comprises:

a chemical-substance sensitive sensor consisting of a potentiometric electrode capable of responding selectively to specific chemical substances, and a liquid-junction type reference electrode including a tube, a porous thread member housed in the front end opening of the tube and having a pore capacity of 0.2 cc/g or more and at least the surface of which is hydrophilic, a silver-silver chloride wire housed in the tube so that at least at its one end the wire is in contact with the thread member and which extends along the tube and is connected to a connector at the other end opening of the tube, an electrical insulating resin filled in said tube at least at the front end portion thereof for fixing both the silver-silver chloride wire and the thread member by contact therewith and for stopping said tube, and an internal solution retained by suction in said porous thread member.

DETAILED DESCRIPTION OF THE INVENTION

Figure 1:
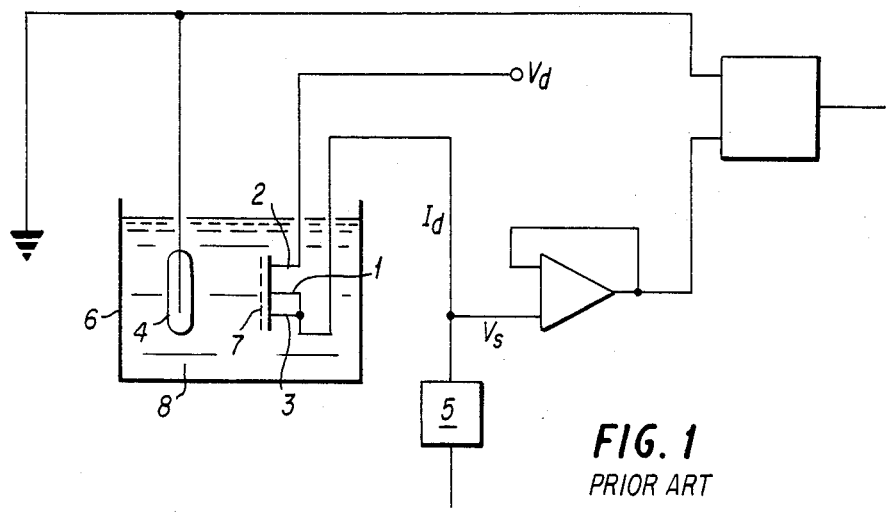
FIG. 1 is a circuit diagram showing an electric circuit for measuring the quantities of chemical substances in a to-be-assayed solution by means of a chemical-substance measuring apparatus including a chemical-substance sensitive sensor using an ISFET as a potentiometric electrode, and a liquid-junction type reference electrode.
Figure 2:
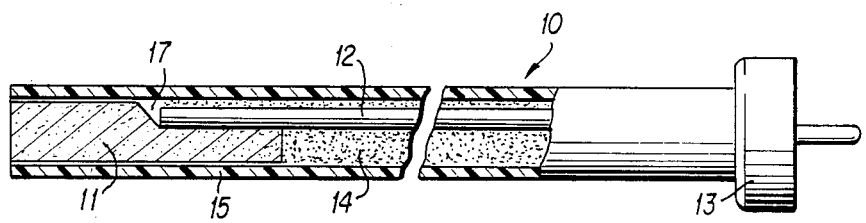
FIGS. 2 and 3 are sectional views showing a liquid-junction type reference electrode used in the chemical-substance measuring apparatus according to the invention.
Figure 3:
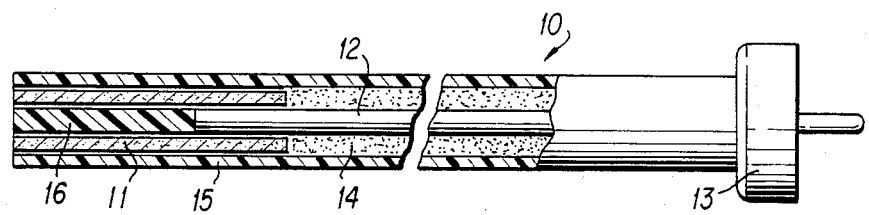

FIGS. 2 and 3 are sections showing a liquid-junction reference electrode employed in a chemical-substance measuring apparatus according to the invention. The reference electrode 10 is used in conjunction with aforesaid potentiometric electrode. The reference electrode comprises a tube 15, a porous thread member 11 housed in the front end opening of the tube and having hydrophilic properties at least with respect to its surface, a silver-silver chloride wire 12 housed in the tube so that at least at its one end the wire is in contact with said thread member and which extends along the tube and is connected to a connector 13 at the other end opening of the tube, an electrical insulating resin filled in said tube at least at the front end portion thereof for fixing both the silver-silver chloride wire and the thread member by contact therewith and for stopping said tube, and an internal solution retained by suction in said porous thread member.

The tube 15 is formed of a waterproof material. For this purpose polyamides, such as Nylon 6, Nylon 11, and Nylon 12, polyesters, polypropylenes, polyvinyl chlorides, and rubbery resins, such as silicone rubbers, urethane rubbers, and polyisoprene rubbers are used.

For the porous thread member housed in the front end opening of the tube and having hydrophilic properties at least on its surface may be used thread materials composed of hydrophilic polymers, e.g., polyvinyl alcohol, ethylene-vinyl alcohol copolymer, hydroxyethyl methacrylate; reaction products of these polymers through reaction with glutaraldehyde, formaldehyde, or the like; and polyacetyl cellulose, and polyacrylonitrile. Also, porous thread materials composed of hydrophobic polymers, such as polypropylene, polytetrafluoroethylene, polyethylene, polystyrene, and polysulfone, and which are hydrophilically surface treated, may be used for the purpose. Among hydrophilic treatment techniques available are sulfonation and the like chemical treatment; and also treatment with ethanol, surface active agent, or the like. Hydrophilication of a porous thread member made of a hydrophobic polymer should be effected to such extent as to allow water to be spontaneously sucked into the pores of the tread member by capillarity. The porous thread member must have a porosity such that its pore capacity is 0.2 cc/g or more to assure that the internal solution is retained in the pores by suction. A pore capacity of less than 0.2 cc/g is undesirable, because it is insufficient to retain the internal solution, which means that the internal resistance of the reference electrode is too large. The term "pore capacity" referred to herein means a value resulting from the division of the total pore capacity (cc) as measured by a mercury penetration porosimeter, by the weight of the sample (g).

The thread member may be a monofilament, multifilament, or staple fiber, in single form as such or in bundle form or in twine form, or it may be in hollow-fiber form. The thread member has pores of $0.01 \sim 10\mu$ each in mean diameter substantially evenly distributed over its cross section. The diametral size of such pore within the range of $0.01 \sim 10\mu$ may vary stepwise or continuously in the inward direction from the fiber surface or in the reverse direction. The thread member may additionally have a very thin skin layer on its surface. If the pore diameter is more than $10\mu$, the mechanical strength of the porous thread member is lower and the diffusion of chlorine ions in the internal solution is faster; and accordingly, the potential of the reference electrode is likely to drift when there occurs a change in the chlorine ion concentration in the solution to be assayed. Conversely, if the pore diameter is less than $0.01\mu$, the diffusion of ions in the internal solution is excessively slow and the internal resistance of the reference electrode is greater, which results in greater induced noise.

For the purpose of reference electrode miniaturization, it is desirable that the outer diameter of the thread member should be as small as possible. Where a hollow fiber is used, one having an outer diameter of $50 \sim 3000\mu$ and a membrane thickness of $10 \sim 500\mu$ is normally used.

The porous thread member mentioned above may be produced by a conventional spinning technique. For example, a polyvinyl alcohol-based porous hollow fiber may be produced by the process disclosed in Japanese Published Unexamined Patent Application No. 21420/1977. A porous polysulfone hollow fiber may be produced by the process disclosed in Japanese Published Unexamined Patent Application No. 91822/1983. By employing these techniques it is possible to continuously produce porous hollow fibers having good heat resistance and high mechanical strength and which can limit the elution of potassium permanganate reducing substances during steam autoclavation to a level below the allowable limit.

The thread member mentioned above is housed in the front end opening of the tube. Desirably, the thread member should be placed in the tube so that its front end is substantially level with the front end of the tube. If the thread member inserted in the tube is too short, the internal solution retained by suction in the thread member may diffuse and flow out into the solution to be assayed. Therefore, the thread member must have such a length that such diffusion and outflow of the internal solution can be reasonably prevented. Such length can be suitably determined according to the configuration of the thread member. In the case of the reference electrode shown in FIG. 2, if the thread member used therein is of a 0.3 mm diameter, for example, the length of the thread member inserted in the tube should usually be more than 1.5 cm. In the case where a hollow fiber 11 is used for the thread member as shown in FIG. 3, it is desirable that a porous monofilament 16 or the like is inserted in the front end opening of the hollow fiber or throughout the length of hollow portion of the fiber in order to close the hollow portion. Where a hollow fiber having an inner diameter of $50\mu$ or less is used, if the front end of the silver-silver chloride wire is spaced apart by more than 2 cm from the liquid junction, any abrupt change in the chlorine ion concentration of the internal solution, that is, any abrupt change in the potential of the silver-silver chloride electrode can be prevented without the necessity of the hollow portion being closed up.

The silver-silver chloride wire housed in the tube must be in contact at its front end with the thread member. In FIG. 2, the silver-silver chloride wire is in contact at its front end with the surface of the thread member. In FIG. 3, the front end of the silver-silver chloride wire is inserted in the hollow portion of the hollow fiber so that its front end is in contact with the inner surface of the hollow fiber. The silver-silver chloride wire extends along the tube and is connected at the other end opening of the tube to the connector. Where a short-length silver-silver chloride wire is used, a lead wire may be connected to one end of the silver-silver chloride wire, the other end of which is in contact with the thread member, so that the lead wire extends along the tube and is connected at the other end opening of the tube to the connector.

For the electrical insulating resin 14 for fixing the silver-silver chloride wire and thread member and for stopping at least the front end portion of the capillary tube, epoxy resin or silicone resin may be used singly or in combination, one with the other.

The internal solution retained by suction in the thread member is usually a saturated KCl solution, if ordinary pH measurement is intended. For the purpose of medical measurements, and more particularly where body fluids, such as blood, are to be assayed, the internal solution is of a composition suitable for the purpose. The internal solution must meet the following conditions:

(1) that the solution is not liable to liquid junction potential difference.

The liquid junction potential difference becomes smaller the closer the mobilities of positive and negative ions moving in the liquid junction at which the solution to be assayed and the thread member are in contact with each other. To meet this condition, it is desirable that the positive and negative ions in the internal solution should be of equal mobility, and that their concentration in the internal solution should be greater than that in the solution to be assayed. Among electrolytes in which the positive and negative ions are equal in mobility are KCl and $NH_4Cl$.

(2) that the internal solution contains no ion to which the ion sensor may respond.

If by any internal solution flowing out from the thread member any change is caused in the ion activity of the solution to be assayed, there should naturally occur errors.

(3) that the internal solution is less likely to react with the solution to be assayed and to cause harm to living bodies.

In the case of blood assaying, the outflow of $K^+$ ion is harmful to the living body. If the internal solution is thicker than the blood, there may occur contraction of blood corpuscles and/or coagulation of proteins because of the difference in penetration pressure. For this reason, and in order to equalize the penetration pressure of the internal solution with that of the blood, physiological salt water (0.15M NaCl solution) is used.

Although $Na^+$ and $Cl^-$ differ from each other in mobility, the salt concentration of the blood is close to 0.15M NaCl and accordingly there will occur no intersolution potential difference.

The aforesaid reference electrode, before it is put in use, is immersed, at its front end portion, in the internal solution so that the internal solution is retained by suction in the thread member. Only after that it is put in use. In this case, suction of the internal solution into the thread member is accomplished by natural suction that exists through the capillarity of micro-pores of the thread member.

The above described reference electrode can be miniaturized. For example, by using a porous thread member having an outer diameter of 0.2 mm and a length of 2 cm, a silver-silver chloride wire having a diameter of 0.1 mm, and a tube of silicone rubber having an inner diameter of 0.3 mm and an outer diameter of 0.4 mm, which is insertible into a living body, it is possible to obtain a very slender reference electrode.

In the above described reference electrode, the internal solution (an electrolyte solution containing chlorine ions) is retained in the micro-pores of the porous thread member, and the porous thread member is held in close contact with the silver-silver chloride electrode and extends up to the liquid junction port; therefore, although it is of a miniature size, there is no possible breakage of electric conductivity between the silver-silver chloride electrode and the solution to be assayed. Even if there should occur any inclusion of bubbles in the space formed at the joint between the silver-silver chloride wire and the thread member (e.g., at 17 in FIG. 2), continuity is constantly held between the silver-silver chloride wire and the solution to be assayed, due to the thread member being in close adhesion, at one end thereof, with the silver-silver chloride wire and contact, at the other end thereof with the solution to be assayed at the liquid junction port. In the pores of the porous thread member there is retained the internal solution by capillarity of the micro-pores, and therefore the breakage of continuity is very unlikely. Even if a plurality of small bubbles should develop in the pores, the individual bubbles are prevented from movement by pore walls; therefore, they are unlikely to grow into bubbles of such size as may break the conductivity between the silver-silver chloride wire and the solution to be assayed. The above described reference electrode uses a prefabricated porous thread member as a holder for the internal solution, and therefore it is very simple to manufacture. In the known type of reference electrode using aforesaid crosslinked polymer gel as a holder for the internal solution, cross-linking reaction takes place only after a solution containing the polymer and a crosslinking agent is poured into the reference electrode. With the known reference electrode, therefore, proper control of crosslinking reaction is difficult and its assembly is very complicated. In contrast to this, the use of a porous filament or yarn, provides several distinct advantages. Since such filament or yarn is produced by spinning techniques on a mass production basis and therefore quantities of such filament or yarn, having uniform performance quality are readily available. Furthermore, where a porous thread member is used as a holder for the internal solution, the liquid junction potential difference involved, if any, is very small as compared with the case where a polymer gel is used. Accordingly, it has also been found that the use of such thread member can minimize measurement errors with the reference electrode. For example, if a hydrophilic polymer sol or gel, in particular, is used as an internal solution holder, there develops an abnormal potential of more than 5 mV in a solution containing borate (e.g., a buffer solution of 9.18 pH), whereas in the case of a porous thread member being used as an internal solution holder, such abnormal potential is reduced to less than 3 mV.

Figure 4:
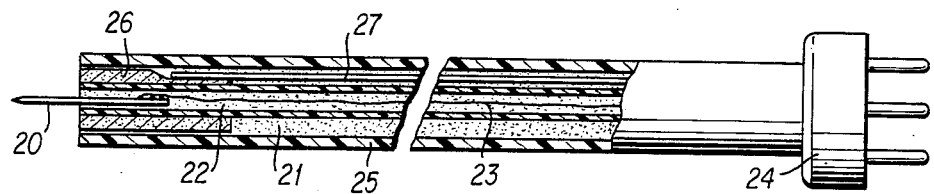
FIGS. 4 and 5 are sections showing another form of the chemical-substance measuring apparatus, in which the chemical-substance sensitive sensor and the liquid-junction reference electrode are housed in one tube.

FIG. 4 illustrates a chemical substance measuring apparatus incorporating a multiple electrode comprising an ISFET and a liquid-junction type reference electrode both housed in one tube. The gate portion of an ISFET 20 projects outwardly from the front end of a first tube 21, and the electrode portion of the ISFET is fixedly buried in a waterproof electrical insulating resin 22 which stops the front end opening of the first tube. A lead wire 23, connected to the electrode portion of the ISFET, extends along the tube and is connected to a connector 24 at an opening of the tube at the other end thereof. The first tube 21 to which the ISFET 20 is fixed is inserted in a second tube 25. A porous hollow fiber 26 is housed in the front end portion of a cavity defined by the two tubes. In the cavity defined by the two tubes there is housed a silver-silver chloride wire 27 which is in contact at its one end with the hollow fiber 26 and which is connected at the other end thereof to the connector 24 at the opening at the other end of the tubes. This electrical insulating resin may be filled in the entire interior space of the first tube and also in the entire cavity defined by the first and second tubes. If an ISFET having a plurality of sensor gates is employed, it is possible to provide an apparatus capable of measuring a plurality of chemical substances.

Figure 5:
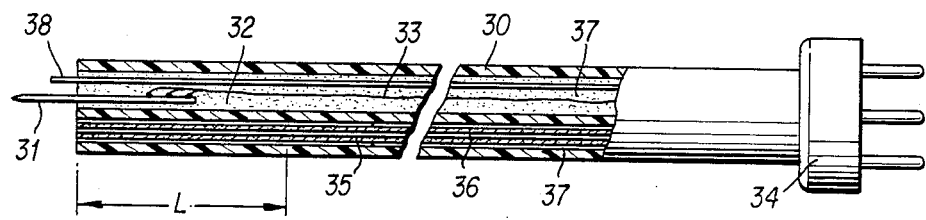

FIG. 5 illustrates an embodiment comprising a tubular body having at least two independent cavities (e.g., a double lumen catheter 30). The gate portion of an ISFET 31 projects from the catheter at the front end of one cavity thereof and the electrode portion of the ISFET is fixedly buried in a waterproof electrical insulating resin 32 which stops the front end opening of the cavity. A lead wire 33, connected to the electrode portion of the ISFET, extends along the cavity and is connected to a connector 34 at the other end opening of the catheter. A porous hollow fiber 35 is housed in another cavity of the catheter at the front end portion thereof. In the hollow space of the hollow fiber there is inserted one end portion of a silver-silver chloride wire 36. The silver-silver chloride wire extends along the cavity and is connected to the connector 34 at the other end of the catheter. In the embodiment of FIG. 5, as shown, a porous hollow fiber is used and there is provided a sufficient length (L) between the front opening of the hollow fiber and the front end of the silver-silver chloride inserted in the hollow space of the hollow fiber; and therefore, the front opening of the hollow fiber is not closed. Further, in FIG. 5, masses of electrical insulating resin 37 are filled in the cavities of the catheter. If a tubular body having three or more independent cavities is employed and a plurality of ISFET's capable of responding selectively to different chemical substances are each housed in one of the cavities, it is possible to provide an apparatus capable of measuring a plurality of chemical substances. A guard electrode 38 is shown which connects the solution to be assayed and a source follower circuit to eliminate alternate-current induced interference and which thereby permit a more accurate measurement. Where an ISFET is used as a potentiometric electrode, alternate-current induced interferences, such as entry into the sensor circuit through a grounding conductor of alternate current from an indoor AC connection or leaking along the floor, may cause fluctuations in the source potential and thus make it difficult to perform accurate measurement of ion concentrations. Especially where a miniaturized liquid-junction type reference electrode embodies the use of high impedance (e.g. 100 K$\Omega$ or more is used) and where the drain current is 30 $\mu$A or below, this alternating current induced interference may be considerable, causing a great effect upon the measurement.

If this guard electrode is connected to an isolation circuit, external signals, chiefly of an alternate current flowing in living bodies, will not flow in the sensor circuit, thereby permitting a constantly accurate measurement. This guard electrode is made of a conductive metal such as platinum or silver. This guard electrode, together with the ISFET, is housed in the cavity. A guard wire, connected to the guard electrode, extends along the cavity and is connected to the connector at the other end of the catheter.

As above described, a porous thread member having a pore capacity of more than 0.2 cc/g and at having it least the surface of which being hydrophilic is used as a holder for the internal solution of the liquid-junction type reference electrode incorporated in the chemical substance measuring apparatus according to the present invention. Accordingly, the liquid-junction type reference electrode in accordance with this invention is free from the possibility of discontinuity between the internal solution and the external solution to be assayed with the assurance of improved stability and accuracy. In addition to its excellent performance characteristics, the reference electrode is easy to assemble and is of a miniaturized type. Therefore, the reference electrode, employed in conjunction with a potentiometric electrode, serves as a very practical chemical substance measuring apparatus for measuring the quantities of chemical substances in a living body.

The following examples and tests are illustrative of this invention:

EXAMPLE 1

First, a porous hollow fiber was produced in accordance with the following procedure. Eight kilograms of polyvinyl alcohol having a mean polymerization degree of 1700, 4 kg of polyethylene glycol having a molecular weight of 1,000, 160 g of boric acid, and 30 g of acetic acid were dissolved into 50 l of hot water. The resulting solution was discharged through an annular nozzle into a coagulating bath containing 80 g/l of caustic acid and 230 g/l of Glauber's salt, and thus a hollow fiber was obtained. The hollow fiber was subjected to crosslinking treatment in a bath containing 0.5 g/l of glutaraldehyde and 3 g/l of hydrochloric acid at 50° C. for 2 hours, then heat treated in hot water at 100° C. for one hour. The hollow fiber so treated was washed in water. The polyvinyl alcohol hollow fiber had an outer diameter of 0.5 mm and an inner diameter of 0.3 mm. An electronographic examination of a section of the hollow fiber showed that there were pores of 0.02~2$\mu$ dia evenly distributed throughout the cross section. The pore capacity of the fiber as determined by a mercury porosimeter was 0.23 cc/g.

Figure 6:
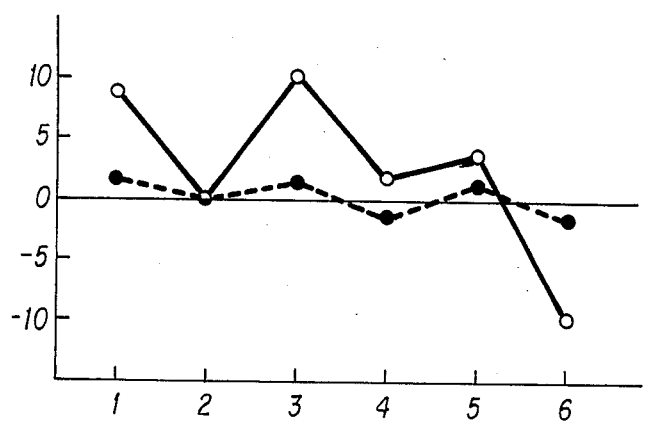
FIG. 6 is a graph showing a performance comparison between the liquid-junction type reference electrode employed in the chemical-substance measuring apparatus of the invention and the conventional liquid-junction type reference electrode.

A silicone rubber tube having an inner diameter of 0.5 mm and an outer diameter of 1.0 mm was swelled with n-hexane, and the above porous polyvinyl alcohol hollow fiber and a silver-silver chloride wire having a diameter of 0.25 mm were inserted into the tube. As illustrated in FIG. 3, the silver-silver chloride wire was inserted in the hollow portion of the hollow fiber. The tube was removed from the n-hexane, and the hexane present thereon was allowed to evaporate under the room temperature conditions. The distance between the front end of the silver-silver chloride wire and the liquid-junction port was fixed at 2 cm. A silicone RTV was poured into the tube through an opening at another end of the tube in FIG. 3, and the silver-silver chloride wire, the hollow fiber, and the silicone rubber tube were fixed. Then, the front end portion of the silicon rubber tube was immersed in a physiological salt water to allow the physiological salt water to be sucked into the hollow fiber by capillarity. For the reference electrode, inter-solution potential difference values were measured with respect to the following six types of solutions: (1) 0.025M $KH_2PO_4$, 0.025M $Na_2HPO_4$; (2) 0.025M $KH_2PO_4$, 0.025M $Na_2HPO_4$, 0.154M NaCl; (3) 0.0087M $KH_2PO_4$, 0.0304M $Na_2HPO_4$; (4) 0.0087M $KH_2PO_4$, 0.0304M $Na_2HPO_4$, 0.154M NaCl; (5) 0.010M $Na_2B_4O_7$; and (6) 0.010M $Na_2BO_7$, 0.154M NaCl. In each solution at 37° C., the potential of the reference electrode was measured with reference to a Radiometer Co. standard electrode (Model K8040). The measurement results are shown by the black dots in FIG. 6. As shown, in these 6 types of solutions, the potential of the reference electrode varies depending chiefly upon the presence or absence of chlorine ion, but the range of such variations is less than approximately 3 mV. The noise level of this reference electrode was about 35 0.2 mV. During steam autoclavation of the reference electrode there was seen no occurrence of discontinuity. When this reference electrode was left to stand for 10 minutes at room temperature, and then bubbles were intentionally included into the interior space of the hollow fiber, there was observed no change in the performance and stability of the reference electrode. Front end portions, 10 cm, of 10 pieces of such reference electrodes were encapsulated, together with 300 ml of water, in a sealed tube and heated at 121° C. for 30 minutes. Then, the internal solutions were withdrawn and subjected to various tests, such as elution test, acute toxicity test, pyrogen test, hemolysis test, and intraskin reaction test. The results of all these tests were found satisfactory.

COMPARATIVE EXAMPLE 1

A porous polyvinyl alcohol hollow fiber was produced in same manner as in Example 1, except that 2 kg of ethylene glycol was used in the spinning solution instead of 4 kg of same. The hollow fiber obtained had a pore capacity of 0.17 cc/g. The outer and inner diameters of the hollow fiber were identical with those in Example 1. By using this hollow fiber was fabricated a reference electrode similar to the one fabricated in Example 1. Inter-solution potential difference measurements made with this electrode showed results similar to those in Example 1. However, this reference electrode gave a noise level of about ±1 mV.

COMPARATIVE EXAMPLE 2

A silver-silver chloride wire having a diameter of 0.25 mm was fixed with silicone RTV in a silicone rubber tube having an inner diameter of 0.5 mm and an outer diameter of 1.0 mm. An aqueous solution containing 5 wt % of polyvinyl alcohol (with a polymerization degree of 1700), 0.5 wt % of titanium lactate as a crosslinking agent, and 0.9 wt % (0.154M) of sodium chloride was injected by a syringe through the end opening of the silicone rubber tube. Then, the composite was allowed to stand overnight in physiological salt water for completion of crosslinking reaction. The potential of the reference electrode relative to that of the standard electrode K8040 was measured in same manner as in Example 1. The measurement results are shown by the white circle dots of FIG. 6. As is apparent from the results shown, this reference electrode is subject to considerable inter-solution changes in potential if the voltage is in the vicinity of 10 mV. Further, when the reference electrode was steam autoclaved, bubbles of same order in size as the inner diameter of the silicone rubber tube were observed in the polyvinyl alcohol, and there developed potential instability.

What is claimed is:

1. A chemical substance measuring apparatus for measuring the quantities of chemical substances contained in a solution to be assayed, said chemical substance measuring apparatus comprising:
   a chemical-substance sensitive sensor having a potentiometric electrode capable of responding selectively to specific chemical substances;
   a liquid-junction type reference electrode comprising:
   a tube,
   a porous thread member housed in a front end opening of said tube wherein said porous thread member has a pore capacity of 0.2 cc/g or more and which has a hydrophilic surface
   a silver-silver chloride wire housed in said tube such that at its one end the wire is in contact with said porous thread member and which extends along said tube and is connected to a connector at the other end opening of said tube,
   an electrical insulating resin filled in said tube at least at the front end portion thereof for fixing both the silver-silver chloride wire and the thread member by contact therewith and for stopping said tube; and
   an internal solution retained by suction in said porous thread member.

2. The apparatus according to claim 1 wherein said potentiometric electrode capable of responding selectively to specific chemical substances is comprised of:
   ion sensitive field effect transistor having a sensor gate.

3. The apparatus according to claim 1 wherein said potentiometric electrode capable of responding selectively to specific chemical substances comprises:
   multiple ion sensitive field effect transistor having a plurality of sensor gates.

4. The apparatus according to claim 1 wherein said porous thread member is a thread-form material comprised:
   of a hydrophilic polymer.

5. The apparatus according to claim 1 wherein said porous thread member is a hollow fiber and wherein the front end portion of the silver-silver chloride wire is inserted in and fixed by the hollow portion of said hollow fiber.

6. The apparatus according to claim 1 wherein said porous hollow fiber is a hollow fiber having a membrane of $10 \sim 500\mu$ in thickness and having micropores of $0.02 \sim 2\mu$ in mean diameter substantially evenly distributed throughout cross section thereof.

7. A chemical substance measuring apparatus for measuring the quantities of chemical substances contained in a solution to be assayed, said chemical substance measuring apparatus comprising:
   a tubular body having at least two independent cavities;
   a chemical-substance sensitive sensor having;

a potentiometric electrode housed in one of said cavities and capable of responding selectively to specific chemical substances, said electrode having a chemical-substance measuring zone projecting outwardly from one end of the tubular body, a lead wire connected at one end thereof to said electrode and extending on the other end side thereof along said cavity, with other end of said lead wire being connected to a connector at an opening of said tubular body at the other end thereof; and an electrical insulating resin filled in said electrode at least at a lead wire junction thereof for stopping the cavity; and a liquid-junction type reference electrode including a porous thread member housed in the front end portion of the other cavity and having a pore capacity of 0.2 cc/g or more and having at least a hydrophilic surface a silver-silver chloride wire housed in said cavity such that one end of said wire is in contact with said thread member and wherein said wire extends along the cavity and is connected to a connector at an opening of the other end of the cavity, an electrical insulating resin filled in said cavity at least at the front end portion thereof, for fixing both the silver-silver chloride wire and the thread member by contact therewith and further for additionally stopping said cavity, and an internal solution retained by suction in the porous thread member.

8. The apparatus according to claim 7 wherein said potentiometric electrode, capable of responding selectively to specific chemical substances, comprises an ion sensitive field effect transistor having a sensor gate.

9. The apparatus according to claim 7 wherein the potentiometric electrode, capable of responding selectively to specific chemical substances, comprises a multiple ion sensitive field effect transistor having a plurality of sensor gates.

10. The apparatus according to claim 7 comprising: a plurality of potentiometric electrodes capable of responding selectively to different chemical substances and wherein each of said potentiometric electrodes are housed in one of the cavities of the tubular body.

11. The apparatus according to claim 7 wherein the porous thread member is a thread-form material comprised of a hydrophilic polymer.

12. The apparatus according to claim 11 wherein said porous thread member is a hollow fiber and wherein the front end portion of the silver-silver chloride wire is inserted in and fixed by the hollow portion of the hollow fiber.

13. The apparatus according to claim 12 wherein said porous hollow fiber is a hollow fiber having a membrane of $10 \sim 500\mu$ in thickness and having fine pores of $0.02 \sim 2\mu$ in mean diameter substantially evenly distributed throughout the cross section thereof.

* * * * *